United States Patent [19]
Gibson et al.

[11] Patent Number: 5,169,973
[45] Date of Patent: Dec. 8, 1992

[54] SYNTHESIS OF ALPHA-AMINONITRILES

[75] Inventors: Harry W. Gibson; Jean-Pierre LeBlanc, both of Blacksburg, Va.

[73] Assignee: Virginia Tech Intellectual Properties, Inc., Blacksburg, Va.

[21] Appl. No.: 685,379

[22] Filed: Apr. 15, 1991

[51] Int. Cl.$^5$ .......................................... C07C 253/30
[52] U.S. Cl. ................... 558/351; 546/330; 548/336.1; 549/74; 549/492; 558/332; 558/408; 558/409; 558/432; 558/433; 558/434; 558/430; 558/452
[58] Field of Search ............... 558/351, 408, 409, 332, 558/430, 452

[56] References Cited
U.S. PATENT DOCUMENTS 4,551,526  11/1985  Mai et al. ............................ 544/163
4,996,346  2/1991  Gibson et al. ...................... 558/392

OTHER PUBLICATIONS

Pandya, et al., Amer. Chem. Soc., Polymer Preprints, 30, pp. 206–207, (1989).
Gibson, et al., Amer. Chem. Soc., Polymer Preprints, 30, pp. 208–209, (1989).
Sanfran, et al., Russ. chem. Rev. 58: pp. 148–162, (1989).
Gassman, et al., Tetrahedron Letters (1978), No. 40, pp. 3773–3776.
Mai, et al., Tetrahedron Letters (1984), 25, No. 41, pp. 4583–4586.
Mai, et al., Synthetic Communications, 15(2), (1985), pp. 157–163.
Mai, et al., Organic Preparations & Procedures Int., 17, (1985), pp. 183–186.

*Primary Examiner*—Joseph P. Brust
*Attorney, Agent, or Firm*—Richard P. Fennelly; Louis A. Morris

[57] ABSTRACT

Alpha-aminonitriles can be synthesized by the reaction, at ambient temperature without use of catalyst, of essentially stoichiometric amounts of amine, aldehyde (either monoaldehyde or dialdehyde) and trimethylsilyl cyanide.

8 Claims, No Drawings

SYNTHESIS OF ALPHA-AMINONITRILES

BACKGROUND OF THE INVENTION

Organic routes for the preparation of aminonitriles are known and one class of reactions involves the formation of the α-trimethylsilyloxy nitrile by the addition of trimethylsilyl cyanide (TMSCN) to an aldehyde in the presence of a Lewis acid, such as zinc iodide. (See, for example, Y. Safran et al., Russ. Chem. Rev., 58:148 (1989); P. G. Gassman et al., Tetrahedron Letters (1978) No. 40, pp. 3773-3776; K. Mai et al., Tetrahedron Letters (1984) 25, No. 41, pp. 4583-4586; and U.S. Pat. No. 4,551,526).

A non-catalytic method for making α-aminonitriles is described by K. Mai et al. in Synthetic Communications, 15(2) 157-163 (1985). This method involves a double stoichiometry of aldehyde or ketone and TMSCN and requires thermal energy. The process entails the heating of two moles of aldehyde or ketone with one mole of amine at 100° C., followed by cooling to room temperature, the addition of two equivalents of TMSCN, and the heating of the resulting reaction mixture to 100° C. again.

In Organic Preparations and Procedures Int., 17, 183-186 (1985) K. Mai et al. proposed use of a somewhat milder reaction that still necessitated the use of thermal energy, i.e., the condensation of the aldehyde and amine in refluxing methanol. This procedure also involved the use of an excess of the aldehyde (33%) and of the TMSCN (100%).

SUMMARY OF THE INVENTION

The present invention relates to the unexpected finding that α-aminonitriles can be prepared at ambient temperature by reacting substantially stoichiometric amounts of an aldehyde, an amine and TMSCN.

DETAILED DESCRIPTION OF THE INVENTION

The aldehyde reactant which can be selected for use herein can be a monoaldehyde having the formula $$R_1CH=O$$

where $R_1$ can be alkyl, cycloalkyl, aralkyl, unsubstituted or substituted aryl, or heteroaryl.

The term "alkyl" as used herein refers to straight or branched chain alkyl radicals containing from 1 to 20 carbon atoms including but not limited to methyl, ethyl, n-propyl, iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl, heptyl, octyl, nonyl, decyl, or cicosyl and the like.

The term "cycloalkyl" as used herein refers to cyclic saturated aliphatic radicals containing 3 to 12 carbon atoms in the ring, such a cyclopropyl, cyclobutyl, cyclopentyl, cyclohexyl, or cyclododecyl.

The term "aryl" represents phenyl or naphthyl which may be unsubstituted or substituted with lower alkyl of from one to about 6 carbon atoms, halo, hydroxy, amino, nitro, lower alkoxy, carboxy, lower alkanoyl, or lower alkoxycarbonyl.

"Heteroaryl" as used herein refers to radicals such as thiophene, furan, pyridine or imidazole, which may be unsubstituted or substituted.

"Substituted aryl or heteroaryl" as used herein refers to aryl or heteroaryl substituted with lower alkyl, lower alkoxy, amido, or halo.

Bis aldehydes of the formula $$HCR'CH \text{ with two } C=O$$

can also be used. $R'$ can be divalent alkylene, arylene, cycloalkylene, substituted arylene or unsubstituted arylene, and heteroarylene analogous to the monovalent $R_1$ groups described above. $R'$ can also be alkylene and arylene groups, optionally separated by heteroatoms, such as oxygen, e.g., arylene-oxygen-alkylene-oxygen-arylene.

Trimethylsilyl cyanide (TMSCN) is a known cyanide source for use in the instant process although it has been used before under differing process conditions as earlier described.

The amine which can be used will be of the formula $$R_2NHR_3$$

where $R_2$ and $R_3$ are independently hydrogen or any of the earlier groups described for $R_1$ above.

The α-aminonitriles which can be synthesized have the formula $$HC(CN)(R_1)N(R_2)(R_3)$$

where $R_1$ to $R_3$ are as defined above.

The instant process represents an improvement over earlier techniques as earlier described. It does not need the presence of a catalyst. The reaction can be run at ambient conditions without heating in a single step. The process can be run without the use of excess reagent (e.g., excess amine or excess TMSCN) (e.g., by adding the amine to the aldehyde/TMSCN mixture, either neat if the aldehyde is a liquid or in an inert solvent if the aldehyde is a solid, or by adding the aldehyde to the amine/TMSCN mixture).

The present invention is further illustrated by the Examples which follow.

EXAMPLE 1

This illustrates the synthesis of N-propyl α-cyanobenzylamine.

To 1.37 gm of benzaldehyde ($12.9 \times 10^{-3}$ mol) and 1.80 ml of trimethylsilyl cyanide ($13.5 \times 10^{-3}$ mol, 5% excess) was added at room temperature 1.15 ml of n-propylamine ($14.0 \times 10^{-3}$ mol) in a closed flask in a nitrogen atmosphere. A very exothermic reaction took place, and the mixture was further stirred for three hours. Then, dichloromethane was added to the mixture, and the organic phase was washed with water ($2 \times 10$ ml). Drying with sodium sulfate and evaporation of the solvent afforded 2.0 gm of an almost pure aminonitrile (yield 90%, containing 3.5% of N-propyl benzilidene).

EXAMPLE 2

This illustrates synthesis of N,N'-bis(propyl)-4,4'-bis-(α-cyano-α-amino)-1,10-di(p-tolyoxy).

The procedure was similar to that shown in Example 1 using p,p'-diformyl-1,10-diphenoxydecane as a bis-aldehyde and twice the stoichiometry of amine and trimethylsilyl cyanide. Similar work up yielded upon evaporation of the solvent to a light yellow solid (yield 95%), a product presenting 5% of aldehyde extremities and 5% of azomethine bonds (crude yield 86%). Recrystallization from ethyl acetate/hexanes afforded a pure, white solid. m. p. 75.2°-77.5° C. (corr.). IR (KBr) : 3323 (NH), 2940, 2920, 2858 (aliph. CH), 2223 (CN), 1614, 1512, 1478 (include C=C ring stretch), 1252 cm$^{-1}$ (C—O—C). $^1$H NMR (CDCl$_3$, 270 MHz) : δ7.40 (d, 4H, Ar—H), 6.90 (d, 4H, ArH), 4.70 (s, 2H, CHCN), 3.95 (t, 4H, CH$_2$O), 2.85-2.65 (m, 4H CH$_2$NH), 1.78 (qn, 4H, CH$_2$—CH$_2$—O), 1.60-1.30 (m, 18H, CH$_2$+NH), 0.95 ppm (t, 6H, CH$_3$). Anal. calc. for C$_{32}$H$_{46}$N$_4$O$_2$: C 74.09, H 8.94, N 10.80; found : C 74.18, H 8.96, N 10.70.

EXAMPLE 3

This illustrates synthesis of bis(α-cyano-α-2-phenethylamino)-1,10-di(p-tolyoxy)decane.

To a closed flask under nitrogen atmosphere containing 4.76 gm of p,p'-diformyl-1,10-diphenoxydecane (1.24×10$^{-2}$ mol) in 30 ml of dichloromethane was added 3.5 ml of trimethylsilyl cyanide (2.62×10$^{-2}$ mol). To the resulting solution was then added 3.3 ml of phenethylamine (2.63×10$^{-2}$ mol). The mixture was stirred for five hours at room temperature and then the solvent was left to partially evaporate overnight by letting nitrogen slowly flow over the reaction mixture. A yellow solid formed, which was filtered and washed three times with hexanes. The resulting white solid was dried under vacuum at room temperature and did not need any further purification (6.7 gm, yield 84%). M. p. 97.1°-98.1° C. (corr). IR (KBr): 3315 cm$^{-1}$ (NH), 3059, 3031 cm$^{-1}$ (arom. CH), 2935, 2919, 2855 cm$^{-1}$ (aliph. CH), 2222 cm$^{-1}$ (CN), 1253 cm$^{-1}$ (C—O—C), 1613, 1513, 832, 748, 700 cm$^{-1}$. $^1$H NMR (CDCl$_3$, 270 MHz): δ7.41-7.34 (d, 4H, Ar—H), 7.35-7.2 (m, 10H, Ar—H of phenethyl moiety), 6.91-6.89 (d, 4H, Ar—H), 4.75 (s, 2H, CH—CN), 3.98-3.91 (t, 4H, CH$_2$O), 3.17-2.96 (m, 4H, CH$_2$NH), 2.92-2.76 (m, 4H, CH$_2$Ar), 1.85-1.70 (qn, 4H, CH$_2$—CH$_2$O), 1.58 (s, 2H, NH), 1.6-1.30 (m, 12H, CH$_2$).

The foregoing illustrate certain embodiments of the present invention but should not be construed in a limiting sense. The scope of protection that is sought is set forth in the claims which follow.

We claim:

1. In a process for the synthesis of an α-aminonitrile which comprises the reaction of amounts of aldehyde, amine and trimethylsilyl cyanide, wherein the improvement comprises conducting the reaction in the absence of catalyst at ambient temperature with substantially equimolar amounts of aldehyde, amine and trimethylsilyl cyanide.

2. A process as claimed in claim 1 wherein the aldehyde is a monoaldehyde and contains an aryl group.

3. A process as claimed in claim 2 wherein benzaldehyde is used.

4. A process as claimed in claim 1 wherein the aldehyde is a dialdehyde.

5. A process as claimed in claim 1 wherein the amine is an n-alkylamine.

6. A process as claimed in claim 2 wherein the amine is an n-alkylamine.

7. A process as claimed in claim 3 wherein the amine is an n-alkylamine.

8. A process as claimed in claim 4 wherein the amine is an n-alkylamine.

* * * * *